(12) United States Patent
Kim et al.

(10) Patent No.: US 12,351,700 B2
(45) Date of Patent: Jul. 8, 2025

(54) PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Yun Ki Cho, Daejeon (KR); Jeong Ju Moon, Daejeon (KR); Joo Ho Kim, Daejeon (KR); Seok Ho Jeong, Daejeon (KR); Woo Hyuk Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 631 days.

(21) Appl. No.: 17/601,871

(22) PCT Filed: Apr. 28, 2020

(86) PCT No.: PCT/KR2020/005592
§ 371 (c)(1),
(2) Date: Oct. 6, 2021

(87) PCT Pub. No.: WO2020/222500
PCT Pub. Date: Nov. 5, 2020

(65) Prior Publication Data
US 2022/0162421 A1    May 26, 2022

(30) Foreign Application Priority Data
May 2, 2019    (KR) .................. 10-2019-0051717

(51) Int. Cl.
*C08K 5/12*    (2006.01)
*C08L 27/06*    (2006.01)

(52) U.S. Cl.
CPC ............. *C08K 5/12* (2013.01); *C08L 27/06* (2013.01)

(58) Field of Classification Search
CPC ...................................................... C08K 5/12
See application file for complete search history.

(56) References Cited

U.S. PATENT DOCUMENTS

| | | | |
|---|---|---|---|
| 3,324,040 A | 6/1967 | Spoor et al. | |
| 2010/0305250 A1 | 12/2010 | Colle et al. | |
| 2016/0237243 A1* | 8/2016 | Woldt | C07C 67/03 |
| 2016/0237244 A1* | 8/2016 | Boeck | C08K 5/12 |
| 2016/0272780 A1 | 9/2016 | Kim et al. | |
| 2016/0376219 A1* | 12/2016 | Kim | C08K 5/12 252/182.28 |
| 2017/0166724 A1 | 6/2017 | Kim et al. | |
| 2018/0163019 A1 | 6/2018 | Kim et al. | |
| 2018/0282512 A1 | 10/2018 | Kim et al. | |

FOREIGN PATENT DOCUMENTS

| | | |
|---|---|---|
| CN | 105102418 A | 11/2015 |
| CN | 105885086 A | 8/2016 |
| CN | 105939991 A | 9/2016 |
| CN | 105940048 A | 9/2016 |
| JP | 5-295207 A | 11/1993 |
| JP | 2017506216 A | 3/2017 |
| JP | 2017509592 A | 4/2017 |
| JP | 2019059888 A | 4/2019 |
| KR | 10-0868194 B1 | 11/2008 |
| KR | 10-2015-0093580 A | 8/2015 |
| KR | 10-2016-0101880 A | 8/2016 |
| KR | 10-2018-0004903 A | 1/2018 |
| KR | 10-1841813 B1 | 5/2018 |
| KR | 10-1973123 B1 | 4/2019 |
| WO | 2009/070398 A1 | 6/2009 |
| WO | 2019039879 A2 | 2/2019 |

OTHER PUBLICATIONS

Database WPI, Week 201919, Thomson Scientific, London, GB, AN 2019-19804G, XP002806486.

* cited by examiner

*Primary Examiner* — Robert C Boyle
(74) *Attorney, Agent, or Firm* — Bryan Cave Leighton Paisner LLP

(57) ABSTRACT

The present disclosure relates to a plasticizer composition characterized in including two or more isophthalates of the same carbon number type, in which alkyl groups bonded to two ester groups have the same carbon number; one or more isophthalates of a different carbon number type, in which alkyl groups bonded to two ester groups have different carbon numbers; wherein the different carbon number type includes both a higher alkyl and a lower alkyl, the carbon number of the higher alkyl is 8 to 10, and the carbon number of the lower alkyl is selected from 5 to 7, thereby, when applied to a resin, showing improved viscosity stability, migration resistance and stress resistance, while maintaining and improving plasticization efficiency and mechanical properties to the same or better level.

7 Claims, No Drawings

PLASTICIZER COMPOSITION AND RESIN COMPOSITION INCLUDING THE SAME

CROSS-REFERENCE TO RELATED APPLICATIONS

The present application is a National Phase entry pursuant to 35 U.S.C. § 371 of International Application No. PCT/KR2020/005592, filed on Apr. 28, 2020, and claims the benefit of and priority to Korean Patent Application No. 10-2019-0051717, filed on May 2, 2019, all of which are hereby incorporated by reference in their entirety for all purposes as if fully set forth herein.

TECHNICAL FIELD

The present invention relates to a plasticizer composition including two or more isophthalates of the same carbon number type and one or more isophthalates of a different carbon number type, and a resin composition including the same.

BACKGROUND ART

Generally, plasticizers are obtained through the reaction of alcohols with polycarboxylic acids such as phthalic acid and adipic acid to form corresponding esters. In addition, considering the internal and external regulations on harmful phthalate-based plasticizers to the human body, studies are being continued on plasticizer compositions which may replace phthalate-based plasticizers such as isophthalate-based, adipate-based and other polymer-based plasticizers.

Meanwhile, regardless of the type of industry including plastisol type of industry of flooring materials, wallpaper, soft and hard sheets, etc., calendaring type of industry, extrusion/injection compound type of industry, the demand for eco-friendly products is increasing. In order to reinforce the quality properties, processability and productivity by the finished products, an appropriate plasticizer is required considering discoloration, migration, mechanical properties, etc.

According to the properties required by the types of industry in various areas of usage, such as tensile strength, elongation rate, light resistance, migration, gelling properties and absorption rate, supplementary materials such as a plasticizer, a filler, a stabilizer, a viscosity decreasing agent, a dispersant, a defoaming agent and a foaming agent are mixed with a PVC resin.

For example, in case of applying di(2-ethylhexyl) isophthalate (DEHIP) which is relatively cheap and widely used among plasticizer compositions which may be applied to PVC, hardness or sol viscosity is high, absorption rate of a plasticizer is relatively slow, and migration and stress migration are not good.

As improvements on the above limitations, the application of a transesterification product with butanol as a plasticizer, as a composition including DEHIP may be considered. In this case, plasticization efficiency is improved but volatile loss, specific gravity, etc. are inferior and mechanical properties are somewhat degraded, and the improvement of physical properties is required. Accordingly, there is no solution but employing a method compensating the defects through mixing with a second plasticizer at the present time.

However, in case of applying the second plasticizer, the change of the physical properties is hard to predict, the application may become a factor of increasing the unit cost of the product, the improvement of the physical properties is not clearly shown except for specific cases, and research thereon is slowly conducted.

DISCLOSURE OF THE INVENTION

Technical Problem

An object of the present invention is to provide a plasticizer composition including two or more isophthalates of the same carbon number type and one or more isophthalates of a different carbon number type, wherein a difference of carbon numbers of alkyl groups bonded to two ester groups of the different carbon number type is 3, thereby showing improved viscosity stability, migration loss and stress resistance, while maintaining and improving plasticization efficiency, volatile loss and mechanical properties to the same or better level when compared with the conventional plasticizer.

Technical Solution

To solve the tasks, according to an embodiment of the present invention, there is provided a plasticizer composition including two or more isophthalates of the same carbon number type, in which alkyl groups bonded to two ester groups have the same carbon number; one or more isophthalates of a different carbon number type, in which alkyl groups bonded to two ester groups have different carbon numbers; wherein the different carbon number type includes both a higher alkyl and a lower alkyl, the carbon number of the higher alkyl is 8 to 10, the carbon number of the lower alkyl is selected from 5 to 7, and a difference of the carbon number between the higher alkyl and the lower alkyl is 3 or less.

To solve the tasks, according to another embodiment of the present invention, there is provided a resin composition including 100 parts by weight of a resin; and 5 to 150 parts by weight of the plasticizer composition.

The resin may be one or more selected from the group consisting of a straight vinyl chloride polymer, a paste vinyl chloride polymer, an ethylene vinyl acetate copolymer, an ethylene polymer, a propylene polymer, polyketone, polystyrene, polyurethane, natural rubber, synthetic rubber and thermoplastic elastomer.

Advantageous Effects

The plasticizer composition according to an embodiment of the present invention, if used in a resin composition, may maintain and improve plasticization efficiency, volatile loss and mechanical properties to the same or better level when compared with the conventional plasticizer, and at the same time, may improve viscosity stability, migration loss and stress resistance.

MODE FOR CARRYING OUT THE INVENTION

It will be understood that terms or words used in the present disclosure and claims should not be interpreted as having a meaning that is defined in common or in dictionaries, however should be interpreted in consistent with the technical scope of the present invention based on the principle that inventors may appropriately define the concept of the terms to explain the invention at his best method.

Definition of Terms

The term "composition" as used in the present disclosure includes a mixture of materials including the corresponding composition as well as a reaction product and a decomposition product formed from the materials of the corresponding composition.

The term "polymer" as used in the present disclosure refers to a polymer compound prepared by polymerizing monomers irrespective of the same or different types. In this way, the general term polymer includes the term homopolymer which is generally used to refer to a polymer prepared by only one type of monomer, and the term interpolymer as defined below.

The term "interpolymer" as used in the present disclosure refers to a polymer prepared by polymerizing at least two types of different monomers. In this way, the general term interpolymer includes generally used copolymer which is generally used to refer to a polymer prepared from two or more different types of monomers, and a polymer prepared from two or more different types of monomers.

The prefix "iso-" as used in the present disclosure means an alkyl group in which a methyl group or an ethyl group is combined as a branched chain with the main chain of the alkyl group, and may be used as a general term of an alkyl group in which a methyl group or an ethyl group is combined as a branched chain with a main chain, including terminal bonding, unless otherwise no separate alkyl group is present in the present disclosure.

The terms "same carbon number type" and "different carbon number type" as used in the present disclosure are terms for classifying isophthalates, wherein the "same carbon number type" means a type in which alkyl groups bonded to two ester groups of an isophthalate have the same carbon number regardless of symmetry or asymmetry, and the "different carbon number type" means a type in which alkyl groups bonded to two ester groups of an isophthalate have different carbon numbers.

The term "straight vinyl chloride polymer" as used in the present disclosure may be one type of vinyl chloride polymers and polymerized by suspension polymerization, bulk polymerization, etc., and may refer to a polymer having a porous particle shape in which a large number of pores having a size of tens to hundreds of micrometers, no cohesiveness, and excellent flowability are dispersed.

The term "paste vinyl chloride polymer" as used in the present disclosure may be one type of vinyl chloride polymers and polymerized by microsuspension polymerization, microseed polymerization, emulsion polymerization, etc., and may refer to a polymer having minute particles without pores and a size of tens to thousands of nanometers, cohesiveness, and inferior flowability.

The terms "comprising", and "having" and the derivatives thereof in the present invention, though these terms are particularly disclosed or not, do not intended to preclude the presence of optional additional components, steps, or processes. In order to avoid any uncertainty, all compositions claimed by using the term "comprising" may include optional additional additives, auxiliaries, or compounds, including a polymer or any other materials, unless otherwise described to the contrary. In contrast, the term "consisting essentially of ~" excludes unnecessary ones for operation and precludes optional other components, steps or processes from the scope of optional continuous description. The term "consisting of ~" precludes optional components, steps or processes, which are not particularly described or illustrated.

Measurement Methods

In the present disclosure, the content analysis of the components in a composition is conducted by gas chromatography measurement using a gas chromatography equipment of Agilent Co. (product name: Agilent 7890 GC, column: HP-5, carrier gas: helium (flow rate of 2.4 ml/min), detector: F.I.D., injection volume: 1 μl, initial value: 70° C./4.2 min, end value: 280° C./7.8 min, program rate: 15° C./min).

In the present disclosure, "hardness" means Shore hardness (Shore "A" and/or Shore "D") at 25° C. and is measured in conditions of 3 T 10 s using ASTM D2240. The hardness may be an index for evaluating plasticization efficiency, and the lower the value is, the better the plasticization efficiency is.

In the present disclosure, "tensile strength" is obtained according to an ASTM D638 method by drawing a specimen in a cross head speed of 200 mm/min (1 T) using a test apparatus of U.T.M (manufacturer: Instron, model name: 4466), measuring a point where the specimen is cut, and calculating according to the following Mathematical Formula 1:

Tensile strength (kgf/cm$^2$)=load value (kgf)/thickness (cm)×width (cm)  [Mathematical Formula 1]

In the present disclosure, "elongation rate" is obtained according to an ASTM D638 method by drawing a specimen in a cross head speed of 200 mm/min (1 T) using the U.T.M, measuring a point where the specimen is cut, and calculating according to the following Mathematical Formula 2:

Elongation rate (%)=length after elongation/initial length×100  [Mathematical Formula 2]

In the present disclosure, "migration loss" is obtained according to KSM-3156, by which a specimen with a thickness of 2 mm or more is obtained, glass plates are attached onto both sides of the specimen and a load of 1 kgf/cm$^2$ is applied. The specimen is stood in a hot air circulation type oven (80° C.) for 72 hours, then taken out therefrom and cooled at room temperature for 4 hours. Then, the glass plates attached onto both sides of the specimen are removed, the weights before and after standing the glass plates and the specimen plate in the oven are measured, and the migration loss is calculated according to Mathematical Formula 3 below.

Migration loss (%)={[(weight of initial specimen)−(weight of specimen after standing in oven)]/(weight of initial specimen)}×100  [Mathematical Formula 3]

In the present disclosure, "volatile loss" is obtained by processing a specimen at 80° C. for 72 hours and then, measuring the weight of the specimen.

Volatile loss (wt %)={[(weight of initial specimen)−(weight of specimen after processing)]/(weight of initial specimen)}×100  [Mathematical Formula 4]

In the present disclosure, "absorption rate" is evaluated by measuring time consumed for mixing a resin and a plasticizer until the torque of a mixer is stabilized by using a planetary mixer (Brabender, P600) in conditions of 77° C. and 60 rpm.

In case of the various measurement conditions, the details of the conditions of the temperature, the speed of revolution, the time, etc., may be somewhat changed according to situations, and if the conditions are different, a measurement method and its conditions are required to be separately indicated.

Hereinafter, the present invention will be explained in more detail to assist the understanding of the present invention.

According to an embodiment of the present invention, a plasticizer composition includes two or more isophthalates of the same carbon number type, in which alkyl groups bonded to two ester groups have the same carbon number;

one or more isophthalates of a different carbon number type, in which alkyl groups bonded to two ester groups have different carbon numbers; wherein the different carbon number type includes both a higher alkyl and a lower alkyl, the carbon number of the higher alkyl is 8 to 10, and the carbon number of the lower alkyl is selected from 5 to 7.

According to an embodiment of the present invention, the plasticizer composition includes the same carbon number type, in which the carbon numbers of alkyl groups bonded to two ester groups are the same, and two or more isophthalates of the same carbon number type.

The same carbon number type means that alkyl groups bonded to two ester groups present in an isophthalate are the same, and the alkyl groups with a benzene ring as a center have the same carbon number, wherein the two isophthalates of the same carbon number type may be classified into a higher alkyl isophthalate having a large carbon number and a lower alkyl isophthalate, and may include both of them at the same time.

As the alkyl groups of the same carbon number type bonded to two ester groups, n-pentyl, isopentyl, n-hexyl, isohexyl, n-heptyl, isoheptyl, 2-ethylhexyl, isononyl, isodecyl or 2-propylheptyl may be included, wherein the type classified into the lower alkyl may be n-pentyl, isopentyl, n-hexyl, isohexyl, n-heptyl and isoheptyl, which have 5 to 7 carbon atoms. In addition, the type classified into the higher alkyl may be 2-ethylhexyl, isononyl, isodecyl and 2-propylheptyl, which have 8 to 10 carbon atoms. Here, if the carbon number of the higher alkyl is less than 8, mechanical properties may be deteriorated, and at the same time, volatile loss and stress resistance may be degraded, and if the higher alkyl having greater than 10 carbon atoms is applied, absorption rate may become very slow, and processing may be impossible, large influence on degrading productivity may be given, plasticization efficiency may also be degraded, and inferior level of physical properties of migration resistance and stress resistance may be shown.

More particularly, the isopentyl, isohexyl and isoheptyl are substituents in which a methyl group or an ethyl group is bonded to a main chain as a branched chain, and for example, the isopentyl may include any one or more of branch type structural isomers of C5 such as 2-methylbutyl, 2,2-dimethylpropyl and 3-methylbutyl, the isohexyl may include one or more among branch type structural isomers of C6 such as 2-methylpentyl, 3-methylpentyl, 4-methylpentyl, 2-ethylbutyl, 2,2-dimethyl butyl and 2,3-dimethyl butyl, and the isoheptyl may include any one or more of branch type structural isomers of C7 such as 2-methylhexyl, 3-methylhexyl, 4-methylhexyl, 5-methylhexyl, 2-ethylpentyl, 3-ethylpentyl, 4-ethylpentyl, and 2,3-dimethylpentyl. Here, if the lower alkyl has less than 5 carbon atoms, it is apprehended that mechanical properties may be deteriorated and at the same time, volatile loss may be degraded, and if a type having less than 7 carbon atoms is applied, defects of deteriorating plasticization efficiency, absorption rate and migration resistance may arise.

The higher alkyl and the lower alkyl are respectively selected if the difference between carbon numbers of the alkyl groups which may be bonded to the lower alkyl isophthalate and the alkyl groups which may be bonded to the higher alkyl isophthalate is 3 or less. In this way, if the difference of the carbon numbers between the lower and higher alkyls is 3 or less and if applied to a resin, the plasticization efficiency may be maintained and improved to the same or better level when compared with a resin having the difference of the carbon numbers of 4, and excellent migration and stress resistance may be shown.

In addition, in another aspect, if applied to a resin, viscosity stability may be significantly excellent, and the improving effects of tensile strength and elongation rate as well as migration may also be excellent when compared with a resin having the difference of the carbon number of 4.

In order to achieve the above-described effects together with the carbon number characteristics of the same carbon number type, an isophthalate of a different carbon number type is required to be included, and in this case, the carbon number difference of alkyl groups bonded to two ester groups of the isophthalate of a different carbon number type may be 3 or less.

Here, two alkyl groups bonded to the ester groups of the isophthalate of a different carbon number type may be the same as the alkyl group of the lower alkyl isophthalate and the alkyl group of the higher alkyl isophthalate of the same carbon number type, respectively, and in case of including an isophthalate of a different carbon number type including all the same alkyl groups in the alkyl groups of the same carbon atom types, the above-mentioned effects may be achieved.

Particularly, the isophthalate of the same carbon number type may be, for example, selected from the group consisting of di(2-propylheptyl) isophthalate, diisodecyl isophthalate, isodecyl(2-propylheptyl) isophthalate, diisononyl isophthalate, di(2-ethylhexyl) isophthalate, di(n-pentyl) isophthalate, diisopentyl isophthalate, (n-pentyl) (isopentyl) isophthalate, di(n-hexyl) isophthalate, diisohexyl isophthalate, isohexyl(n-hexyl) isophthalate, di(n-heptyl) isophthalate, diisoheptyl isophthalate and isoheptyl(n-heptyl) isophthalate.

In addition, the same carbon number type may have the same carbon number of mutual alkyl groups and the same structure thereof, but according to circumstances, an isophthalate having the same carbon number but different structures, i.e., an isophthalate including alkyl groups having a relationship of structural isomers, may be included.

Such an isophthalate of the same carbon number type may be, for example, isodecyl(2-propylheptyl) isophthalate, isohexyl(n-hexyl) isophthalate, isoheptyl(n-heptyl) isophthalate and (n-pentyl)(isopentyl) isophthalate.

In addition, the isophthalate of a different carbon number type may be, for example, selected from the group consisting of (n-pentyl)(2-ethylhexyl) isophthalate, (isopentyl)(2-ethylhexyl) isophthalate, (2-methylbutyl) (2-ethylhexyl) isophthalate, (n-hexyl) (2-ethylhexyl) isophthalate, isohexyl (2-ethylhexyl) isophthalate, (n-heptyl)(2-ethylhexyl) isophthalate, isoheptyl(2-ethylhexyl) isophthalate, (n-pentyl) (isononyl) isophthalate, (isopentyl) (isononyl) isophthalate, (n-hexyl) (isononyl) isophthalate, isohexyl(isononyl) isophthalate, (n-heptyl) (isononyl) isophthalate, isoheptyl (isononyl) isophthalate, (n-pentyl) (isodecyl) isophthalate, (isopentyl) (isodecyl) isophthalate, (n-hexyl) (isodecyl) isophthalate, isohexyl(isodecyl) isophthalate, (n-heptyl) (isononyl) isophthalate, isoheptyl(isodecyl) isophthalate, (n-pentyl)(2-propylheptyl) isophthalate, (isopentyl)(2-propylheptyl) isophthalate, (n-hexyl) (2-propylheptyl) isophthalate, isohexyl(2-propylheptyl) isophthalate, (n-heptyl)(2-propylheptyl) isophthalate, and isoheptyl(2-propylheptyl) isophthalate.

The plasticizer composition according to an embodiment of the present invention includes the same carbon number type and the different carbon number type as the isophthalates as described above, and due to factors such as the number of isophthalates of each type, the kind of alkyl groups bonded, and the carbon number difference between alkyl groups bonded, the physical properties such as migration resistance and stress resistance may be improved, furthermore, the viscosity stability of a resin may be enhanced, and plasticization efficiency or mechanical properties may be maintained and improved to levels exceeding those of the conventional products.

According to an embodiment of the present invention, the plasticizer composition may have the moisture content with respect to the total weight of the composition of 500 ppm or less, preferably, 300 ppm or less, more preferably, 100 ppm or less based on a weight. If the moisture content in the plasticizer is high, the possibility of degenerating the plasticizer due to surrounding environmental factors is high and the possibility of generating defects during processing is high, and accordingly, the lower moisture contents in the plasticizer are more desirable.

According to an embodiment of the present invention, the isophthalate of the same carbon number type and the isophthalate of a different carbon number type, included in the plasticizer composition may be included in a ratio of 95:5 to 30:70 by a weight ratio. If the isophthalates are included in the aforementioned ranges, the improving effects of the above-described migration resistance, stress resistance and viscosity stability may be achieved, and the improvement of mechanical properties and plasticization efficiency may also be expected.

More particularly, if the isophthalate included in the plasticizer composition includes three types of a lower alkyl isophthalate, an isophthalate of a different carbon number type and a higher alkyl isophthalate, each may be included in 0.5 to 50 wt %, 3.0 to 70 wt % and 0.5 to 85 wt % based on the total weight of the plasticizer composition, and these amounts are values in case where the total sum of the three kinds of the isophthalates is considered 100 wt %, but a case where another material is included in the plasticizer composition is not considered.

As described above, if the above-described amounts are satisfied, effects obtainable from the isophthalate of a different carbon number type, which has a carbon number difference of 3 or less, may be more preferably achieved, and the reproducibility of the effects may also be excellent.

Further, considering the optimization of such effects, the amounts of the three kinds of the isophthalates may preferably be 0.5 to 50 wt %, 10 to 50 wt %, and 35 to 80 wt %.

The method for preparing the plasticizer composition according to an embodiment of the present invention is a well-known method in the art, and any methods may be applied without specific limitation only if the above-described plasticizer composition is prepared.

Particularly, for the above-described plasticizer composition, one including three kinds of isophthalates is a basic, and an esterification reaction may be used and transesterification reaction as well as direct esterification reaction may be applied.

For example, the direct esterification reaction may be performed by a step of injecting isophthalic acid and two or more kinds of alcohols, adding a catalyst and reacting under a nitrogen atmosphere; a step of removing unreacted alcohol and neutralizing unreacted acid; and a step of dehydrating by distillation under a reduced pressure and filtering.

The alcohol may include one or more lower alkyl alcohols selected from the group consisting of n-pentyl alcohol, isopentyl alcohol, n-hexyl alcohol, isohexyl alcohol, n-heptyl alcohol and isoheptyl alcohol, and as a higher alkyl alcohol, one or more selected from 2-ethylhexyl alcohol, isononyl alcohol, isodecyl alcohol and 2-propylheptyl alcohol may be applied. The alcohol may be used in a range of 150 to 500 mol %, 200 to 400 mol %, 200 to 350 mol %, 250 to 400 mol %, or 270 to 330 mol % based on 100 mol % of the isophthalic acid.

The catalyst may be, for example, one or more selected from an acid catalyst such as sulfuric acid, hydrochloric acid, phosphoric acid, nitric acid, paratoluenesulfonic acid, methanesulfonic acid, ethanesulfonic acid, propanesulfonic acid, butanesulfonic acid, and alkyl sulfate, a metal salt such as aluminum lactate, lithium fluoride, potassium chloride, cesium chloride, calcium chloride, iron chloride, and aluminum phosphate, a metal oxide such as heteropoly acids, natural/synthetic zeolites, cation and anion exchange resins, and an organometal such as tetra alkyl titanate and the polymers thereof. In a particular embodiment, the catalyst may use tetra alkyl titanate.

The amount used of the catalyst may be different according to the type thereof, and for example, a homogeneous catalyst may be used in an amount of 0.01 to 5 wt %, 0.01 to 3 wt %, 1 to 5 wt % or 2 to 4 wt % based on total 100 wt % of reactants, and a heterogeneous catalyst may be used in an amount of 5 to 200 wt %, 5 to 100 wt %, 20 to 200 wt %, or 20 to 150 wt % based on the total amount of reactants.

In this case, the reaction temperature may be within a range of 180 to 280° C., 200 to 250° C., or 210 to 230° C.

In another embodiment, the transesterification reaction may prepare an isophthalate compound through transesterification reaction by which a high alkyl isophthalate among the same carbon number type such as di(2-ethylhexyl) isophthalate and a lower alkyl alcohol which is an alcohol having an alkyl group corresponding to a lower alkyl. Here, the alkyl groups included in the isophthalate and the alcohol may be exchanged, and if two or more types of alcohols are used in the transesterification reaction, the reaction products may be total six isophthalate types, for example, four same carbon number types, and two different carbon number types may be formed. The same carbon number type may include three types of lower alkyl isophthalates and one type of higher alkyl isophthalate.

"Transesterification" used in the present invention means the reaction of an alcohol and an ester as shown in Reaction 1 below to interchange R" of the ester with R' of the alcohol as shown in Reaction 1 below.

[Reaction 1]

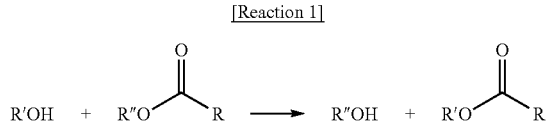

According to an embodiment of the present invention, if the transesterification is carried out, three kinds of ester compositions may be produced according to three cases: a case where the alkoxide of the alcohol attacks the carbon of two ester groups (RCOOR") which are present in the ester-based compound; a case where the alkoxide of the alcohol attacks the carbon of one ester group (RCOOR") which is present in the ester-based compound; and a unreacted case wherein no reaction is performed.

In addition, the transesterification has advantages of not generating wastewater problems when compared with the esterification between acid-alcohol, being performed without a catalyst and solving defects occurring when using an acid catalyst.

The composition ratio of the mixture prepared through the transesterification may be controlled according to the addition amount of the alcohol. The amount added of the alcohol may be 0.1 to 89.9 parts by weight, particularly, 3 to 50 parts by weight, more particularly, 5 to 40 parts by weight based on 100 parts by weight of the isophthalate compound.

In regard of the isophthalate compound, since the mole fraction of the isophthalate which participates in the transesterification may increase according to the increase of the amount added of the alcohol, the amounts of two isophthalates which are products in the mixture may increase, and correspondingly, the amount of the isophthalate which is present as an unreacted state, may tend to decrease.

According to an embodiment of the present invention, the molar ratio of the reactants, isophthalate and alcohol may be, for example, 1:0.005 to 5.0, 1:0.05 to 2.5, or 1:0.1 to 1.0, and within this range, processing efficiency and economic feasibility may be excellent, and a plasticizer composition capable of achieving the above-described effects may be obtained.

According to an embodiment of the present invention, the transesterification may be performed at a reaction temperature of 120° C. to 190° C., preferably, 135° C. to 180° C., more preferably, 141° C. to 179° C. for 10 minutes to 10 hours, preferably, 30 minutes to 8 hours, more preferably, 1 to 6 hours. Within the temperature and time ranges, the composition ratio of a final plasticizer composition may be efficiently controlled. In this case, the reaction time may be calculated from a point when the reaction temperature is achieved after elevating the temperature of the reactants.

The transesterification may be performed under an acid catalyst or a metal catalyst, and in this case, the effects of decreasing the reaction time may be achieved.

The acid catalyst may include, for example, sulfuric acid, methanesulfonic acid or p-toluenesulfonic acid, and the metal catalyst may include, for example, an organometal catalyst, a metal oxide catalyst, a metal salt catalyst, or a metal itself.

The metal component may be, for example, any one selected from the group consisting of tin, titanium and zirconium, or a mixture of two or more thereof.

In addition, a step of removing unreacted alcohol and reaction by-products by distillation may be further included after the transesterification. The distillation may be, for example, a two-step distillation by which the alcohol and the by-products are individually separated using the difference of the boiling points. In another embodiment, the distillation may be mixture distillation. In this case, effects of relatively stable securing of an ester-based plasticizer composition in a desired composition ratio may be achieved. The mixture distillation means distillation of the unreacted alcohol and the by-products simultaneously.

According to another embodiment of the present invention, a resin composition including the plasticizer composition and a resin is provided.

The resin may use resins well-known in the art. For example, a mixture of one or more selected from the group consisting of a straight vinyl chloride polymer, a paste vinyl chloride polymer, an ethylene vinyl acetate copolymer, an ethylene polymer, a propylene polymer, polyketone, polystyrene, polyurethane, natural rubber, synthetic rubber and thermoplastic elastomer may be used, without limitation.

The plasticizer composition may be included in 5 to 150 parts by weight, preferably, 5 to 130 parts by weight, or 10 to 120 parts by weight based on 100 parts by weight of the resin.

Generally, the resin using the plasticizer composition may be prepared into a resin product through a melt processing or a plastisol processing, and a resin by the melt processing and a resin from the plastisol processing may be produced differently according to each polymerization method.

For example, in case of using a vinyl chloride polymer in a melt processing, solid phase resin particles having a large average particle diameter are prepared by suspension polymerization, or the like and used, and the vinyl chloride polymer is referred to as a straight vinyl chloride polymer. In case of using a vinyl chloride polymer in a plastisol processing, a sol state resin as minute resin particles are prepared by emulsion polymerization, or the like and used, and this vinyl chloride polymer is referred to as a paste vinyl chloride resin.

In case of the straight vinyl chloride polymer, a plasticizer may be included in a range of 5 to 80 parts by weight with respect to 100 parts by weight of the polymer, and in case of the paste vinyl chloride polymer, the plasticizer may be included in a range of 40 to 120 parts by weight with respect to 100 parts by weight of the polymer.

The resin composition may further include a filler. The filler may be 0 to 300 parts by weight, preferably, 50 to 200 parts by weight, more preferably, 100 to 200 parts by weight based on 100 parts by weight of the resin.

The filler may use fillers well-known in the art and is not specifically limited. For example, the filler may be a mixture of one or more kinds selected from silica, magnesium carbonate, calcium carbonate, hard coal, talc, magnesium hydroxide, titanium dioxide, magnesium oxide, calcium hydroxide, aluminum hydroxide, aluminum silicate, magnesium silicate and barium sulfate.

In addition, the resin composition may further include other additives such as a stabilizer as necessary. Each of the other additives such as the stabilizer may be, for example, 0 to 20 parts by weight, preferably, 1 to 15 parts by weight based on 100 parts by weight of the resin.

The stabilizer may use, for example, a calcium-zinc-based (Ca—Zn-based) stabilizer such as a composite stearate of calcium-zinc or a barium-zinc-based (Ba—Zn-based) stabilizer, but is not specifically limited.

The resin composition may be applied to both a melt processing and a plastisol processing as described above, and a calendaring processing, an extrusion processing, or an injection processing may be applied to the melt processing, and a coating processing, or the like may be applied to the plastisol processing.

EXAMPLES

Hereinafter, embodiments will be explained in detail to particularly explain the present invention. The present invention may, however, be embodied in different forms and should not be construed as limited to the embodiments set forth herein. Rather, these embodiments are provided so that this disclosure will be thorough and complete, and will fully convey the scope of the inventive concept to those skilled in the art.

Example 1

To a reactor equipped with a stirrer, a condenser and a decanter, 2000 g of di(2-ethylhexyl) isophthalate (GL300, LG Chem), and 340 g of n-pentyl alcohol (17 parts by weight based on 100 parts by weight of DEHIP) were injected, and transesterification was carried out under a nitrogen atmosphere at a reaction temperature of 160° C. for 2 hours to obtain a composition including di(n-pentyl) isophthalate (DnPIP), (n-pentyl)(2-ethylhexyl) isophthalate (nPEHIP) and di(2-ethylhexyl) isophthalate (DEHIP) in amounts of 3.6 wt %, 31.7 wt % and 64.7 wt %, respectively.

Examples 2 to 7

Compositions of three components having weight ratios described in Table 1 were obtained by the same method as in Example 1 except for applying alcohols corresponding to lower alkyls described in Table 1 instead of the n-pentyl alcohol.

Example 8

A composition of three components having a weight ratio described in Table 1 was obtained by the same method as in Example 1 except for using n-hexyl alcohol instead of the n-pentyl alcohol and using diisononyl isophthalate instead of the di(2-ethylhexyl) isophthalate.

Comparative Example 1

Diisononyl phthalate (DINP), a product of LG Chem, was used as a plasticizer composition.

Comparative Example 2

Di(2-ethylhexyl) terephthalate (DEHTP, LGflex GL300), a product of LG Chem, was used as a plasticizer composition.

Comparative Examples 3 to 7

Compositions of three components having weight ratios described in Table 1 were obtained by the same method as in Example 1 except for using alcohols corresponding to lower alkyls described in Table 1 instead of the n-pentyl alcohol and using dialkyl terephthalate to which alkyls corresponding to higher alkyls described in Table 1 were bonded instead of the di(2-ethylhexyl) terephthalate.

TABLE 1

|  | Lower alkyl | Higher alkyl | Lower non-mixed | Mixed | Higher non-mixed |
|---|---|---|---|---|---|
| Example 1 | n-pentyl | 2-ethylhexyl | 3.6 | 31.7 | 64.7 |
| Example 2 | 2-methylbutyl | 2-ethylhexyl | 2.5 | 27.4 | 70.1 |
| Example 3 | n-hexyl | 2-ethylhexyl | 4.1 | 32.2 | 63.7 |
| Example 4 | 2-ethylbutyl | 2-ethylhexyl | 4.2 | 32.9 | 62.9 |
| Example 5 | n-heptyl | 2-ethylhexyl | 7.8 | 40.0 | 52.2 |
| Example 6 | 5-methylhexyl | 2-ethylhexyl | 8.0 | 41.1 | 50.9 |
| Example 7 | n-pentyl | 2-ethylhexyl | 6.5 | 39.5 | 54.0 |
| Example 8 | n-hexyl | isononyl | 12.3 | 42.7 | 45.0 |
| Comparative Example 3 | n-butyl | 2-ethylhexyl | 6.0 | 38.1 | 55.9 |
| Comparative Example 4 | n-pentyl | Isononyl | 7.4 | 39.5 | 53.1 |
| Comparative Example 5 | 2-ethylhexyl | 2-propylheptyl | 41.2 | 46.1 | 12.7 |
| Comparative Example 6 | n-butyl | n-heptyl | 4.8 | 32.0 | 63.2 |
| Comparative Example 7 | 2-methylbutyl | n-heptyl | 5.8 | 38.5 | 55.7 |

* The contents are all wt %.

Experimental Examples: Evaluation of Performance

By using the plasticizers of the Examples and Comparative Examples, specimens were manufactured according to ASTM D638 and the prescription and manufacturing conditions below.

(1) Prescription:
  100 parts by weight of a straight vinyl chloride polymer (LS100S), 30 parts by weight of a plasticizer and 3 parts by weight of a stabilizer (BZ-153T)
(2) Mixing:
  mixing at 98° C. in 700 rpm
(3) Manufacture of Specimen:
  1 T and 3 T sheets were manufactured by processing at 160° C. for 4 minutes by a roll mill, and at 180° C. for 2.5 minutes (low pressure) and 2 minutes (high pressure) by a press
(4) Test Items
1) Hardness:
  Shore hardness (Shore "A" and "D") at 25° C. was measured using a 3 T specimen for 10 seconds using ASTM D2240. The plasticization efficiency was assessed excellent if the value was small.
2) Tensile Strength:
  By an ASTM D638 method, a specimen was drawn in a cross-head speed of 200 mm/min using a test apparatus of U.T.M (manufacturer: Instron, model name: 4466), and a point where the 1 T specimen was cut was measured. The tensile strength was calculated as follows.

Tensile strength $(kgf/cm^2)$=load value (kgf)/thickness (cm)×width (cm)

3) Elongation Rate Measurement:
  By an ASTM D638 method, a specimen was drawn in a cross-head speed of 200 mm/min using a test apparatus of U.T.M, and a point where the 1 T specimen was cut was measured. The elongation rate was calculated as follows.

Elongation rate (%)=length after elongation/initial length×100

4) Migration Loss Measurement:
  Glass plates were attached onto both sides of a 1 T specimen, and a load of 1 $kgf/cm^2$ was applied. The specimen was stood in a hot air circulation type oven (80° C.) for 72 hours and then taken out and cooled at room temperature for 4 hours. Then, glass plates attached onto both sides of the specimen were removed, and weights before and after standing the glass plates and the specimen plate in the oven were measured, and the migration loss was calculated as follows.

Migration loss (%)={[(weight of initial specimen)−(weight of specimen after standing in oven)]/(weight of initial specimen)}×100

5) Volatile Loss Measurement:
  The specimen manufactured was processed at 80° C. for 72 hours, and the weight of the specimen was measured.

Volatile loss (wt %)={[(weight of initial specimen)−(weight of specimen after processing)]/(weight of initial specimen)}×100

6) Stress Test (Stress Resistance):
  A specimen with a thickness of 2 mm in a bent state was stood at 23° C. for 72 hours, and the degree of migration (degree of oozing) was observed. The results were recorded as numerical values (by 0.5 unit from 0 to 3), and excellent properties were shown if the value was closer to 0.
7) Absorption Rate Measurement
  Absorption rate was evaluated by measuring the time consumed for mixing a resin and an ester compound and stabilizing the torque of a mixer by using a planetary mixer (Brabender, P600) in conditions of 77° C. and 60 rpm.
8) Light Resistance Measurement
  By a method of ASTM 4329-13, the specimen was put on QUV (QUV/se, Q-LAB) and exposed to UV (340 nm) for 200 hours, and color change (ΔE) was confirmed using Reflectometer (Tintometer, LoviBond).

(5) Evaluation Results

The evaluation results on the test items are listed in Table 2 and 3 below.

TABLE 2

|  | Hardness (Shore A) | Hardness (Shore D) | Tensile strength (kgf/cm2) | Elongation rate (%) | Migration loss (%) | Volatile loss (%) |
|---|---|---|---|---|---|---|
| Example 1 | 92.5 | 47.2 | 256.9 | 301.2 | 2.99 | 1.69 |
| Example 2 | 92.9 | 48.6 | 251.2 | 294.4 | 2.91 | 1.77 |
| Example 3 | 92.7 | 48.1 | 255.5 | 300.7 | 3.07 | 1.14 |
| Example 4 | 93.2 | 48.9 | 263.4 | 298.0 | 2.90 | 1.42 |
| Example 5 | 93.0 | 48.4 | 259.9 | 294.9 | 3.11 | 1.02 |
| Example 6 | 93.2 | 48.7 | 260.4 | 302.1 | 3.15 | 1.10 |
| Example 7 | 91.6 | 46.2 | 267.8 | 295.8 | 2.13 | 1.80 |
| Example 8 | 93.5 | 49.2 | 241.7 | 290.3 | 3.54 | 0.87 |
| Comparative Example 1 | 93.9 | 49.7 | 230.3 | 280.9 | 2.32 | 0.75 |
| Comparative Example 2 | 94.8 | 50.1 | 249.9 | 301.5 | 4.57 | 0.78 |
| Comparative Example 3 | 91.5 | 47.3 | 238.1 | 289.0 | 3.87 | 3.88 |
| Comparative Example 4 | 94.3 | 49.9 | 233.3 | 290.2 | 4.32 | 1.58 |
| Comparative Example 5 | 95.4 | 51.8 | 235.3 | 302.4 | 4.30 | 0.78 |
| Comparative Example 6 | 90.3 | 45.5 | 230.6 | 284.7 | 3.53 | 3.51 |
| Comparative Example 7 | 90.4 | 45.7 | 235.4 | 288.3 | 3.65 | 3.74 |

TABLE 3

|  | Stress migration | Absorption rate | Light resistance |
|---|---|---|---|
| Example 1 | 1.0 | 5 m 10 s | 1.05 |
| Example 2 | 1.0 | 6 m 12 s | 1.07 |
| Example 3 | 1.0 | 5 m 58 s | 0.98 |
| Example 4 | 1.0 | 5 m 60 s | 0.85 |
| Example 5 | 1.5 | 6 m 10 s | 1.02 |
| Example 6 | 1.5 | 6 m 15 s | 1.12 |
| Example 7 | 1.0 | 4 m 45 s | 1.10 |
| Example 8 | 1.0 | 6 m 02 s | 1.00 |
| Comparative Example 1 | 0.5 | 4 m 30 s | 1.10 |
| Comparative Example 2 | 3.0 | 7 m 56 s | 3.25 |
| Comparative Example 3 | 1.0 | 4 m 25 s | 1.14 |
| Comparative Example 4 | 1.5 | 5 m 55 s | 1.25 |
| Comparative Example 5 | 3.0 | 8 m 26 s | 1.35 |
| Comparative Example 6 | 3.0 | 4 m 40 s | 1.01 |
| Comparative Example 7 | 3.0 | 4 m 50 s | 1.14 |

Referring to the results of Tables 2 and 3, it could be confirmed that the cases where the plasticizers of Examples 1 to 8 were applied showed excellent effects regarding most physical properties, excellent balance between physical properties, and particularly excellent effects regarding tensile strength, elongation rate, stress resistance and plasticization efficiency when compared with the cases of applying the plasticizers of Comparative Examples 1 to 7. Further, the absorption rate was between 4 minutes to 6 minutes and was not so fast, and there were no worries on discharging. Considering that the absorption rate did not exceed 7 minutes, it could be confirmed that processability also was excellent. Particularly, it could be confirmed that mechanical properties were markedly improved when compared with Comparative Example 1 in which the conventional commercial plasticizer product was used, and performance was good but environmental issues were present. Also, it could be confirmed that plasticization efficiency, migration loss, stress resistance and light resistance were very excellent, and absorption rate could be improved to a suitable level when compared with Comparative Example 2 which corresponded to the conventional eco-friendly product.

In addition, different from the plasticizer composition according to the present invention, Comparative Example 3 in which the difference of the carbon numbers between the higher alkyl and lower alkyl was not 3 or less, and the carbon number of the lower alkyl was less than 5, showed particularly inferior elongation rate and volatile loss, and Comparative Example 4 in which the carbon numbers of the lower alkyl and the higher alkyl were the same as those of the present invention, but the difference of the carbon numbers was still greater than 3, showed deteriorated plasticization efficiency and tensile strength and inferior migration loss.

In addition, it was confirmed that Comparative Example 5 in which the difference of the carbon numbers was satisfied, but the carbon number of the lower alkyl was too large, showed a significant loss of plasticization efficiency, too slow absorption rate, very poor processability, and inferior migration resistance and stress resistance. Further, if the carbon numbers of the higher alkyl and the carbon number of the lower were all small, tensile strength, elongation rate, volatile loss and stress resistance were all deteriorated as confirmed in Comparative Example 6, and the same effects could be confirmed in Comparative Example 7 in which the carbon number of the higher alkyl was small.

The invention claimed is:

1. A plasticizer composition, comprising:
    two or more of a same carbon number type isophthalate, which is an isophthalate in which alkyl groups bonded to two ester groups have the same carbon number;
    one or more of a different carbon number type isophthalate, which is an isophthalate in which alkyl groups bonded to two ester groups have different carbon numbers;
    wherein the different carbon number type isophthalate comprises both a higher alkyl and a lower alkyl, the carbon number of the higher alkyl is 8 to 9, and the carbon number of the lower alkyl is 5 to 7,
    wherein a difference of the carbon number between the higher alkyl and the lower alkyl is 3 or less, and
    wherein, based on a total weight of the plasticizer composition, the plasticizer composition comprises:
    2.5 to 12.3 wt % of the lower alkyl isophthalate;
    27.4 to 42.7 wt % of the different carbon number type isophthalate; and
    45.0 to 70.1 wt % of the higher alkyl isophthalate.

2. The plasticizer composition according to claim 1, wherein the two or more of the same carbon number type isophthalate comprise a higher alkyl isophthalate having an alkyl of 8 to 9 carbon numbers and a lower alkyl isophthalate having an alkyl of 5 to 7 carbon numbers.

3. The plasticizer composition according to claim 1, wherein the different carbon number type isophthalate is one or more selected from the group consisting of (n-pentyl) (2-ethylhexyl) isophthalate, (isopentyl) (2-ethylhexyl) isophthalate, (n-hexyl) (2-ethylhexyl) isophthalate, isohexyl (2-ethylhexyl) isophthalate, (n-heptyl) (2-ethylhexyl) isophthalate, isoheptyl(2-ethylhexyl) isophthalate, (n-pentyl)(isononyl) isophthalate, (isopentyl) (isononyl) isophthalate, isohexyl(isononyl) isophthalate, (n-heptyl) (isononyl) isophthalate, isoheptyl(isononyl) isophthalate and (n-heptyl) (isononyl) isophthalate.

4. The plasticizer composition according to claim 1, wherein the same carbon number type isophthalate is two or more selected from the group consisting of diisononyl isophthalate, di(2-ethylhexyl) isophthalate, di(n-pentyl) isophthalate, diisopentyl isophthalate, (n-pentyl) (isopentyl) isophthalate, di(n-hexyl) isophthalate, diisohexyl isophthalate, isohexyl(n-hexyl) isophthalate, di(n-heptyl) isophthalate, diisoheptyl isophthalate and isoheptyl(n-heptyl) isophthalate.

5. The plasticizer composition according to claim 1, wherein a weight ratio of the two or more of the same carbon number type isophthalate to the one or more of the different carbon number type isophthalate is 95:5 to 30:70.

6. A resin composition, comprising:
   100 parts by weight of a resin; and
   5 to 150 parts by weight of the plasticizer composition according to claim 1.

7. The resin composition according to claim 6, wherein the resin is one or more selected from the group consisting of a straight vinyl chloride polymer, a paste vinyl chloride polymer, an ethylene vinyl acetate copolymer, an ethylene polymer, a propylene polymer, polyketone, polystyrene, polyurethane, natural rubber, synthetic rubber and thermoplastic elastomer.

\* \* \* \* \*